United States Patent
Yagihashi et al.

(12)

(10) Patent No.: US 6,667,415 B1
(45) Date of Patent: Dec. 23, 2003

(54) TERTIARY BUTYL 4,4-BIS(4'-HYDROXYPHENYL) PENTANOATE DERIVATIVES AND POSITIVE RESIST MATERIALS CONTAINING THE SAME

(75) Inventors: Fujio Yagihashi, Yokohama (JP); Jun Watanabe, Kawasaki (JP); Minoru Takamizawa, Setagaya-ku (JP); Akinobu Tanaka, Atsugi (JP); Yoshio Kawai, Isehara (JP); Tadahito Matsuda, Atsugi (JP)

(73) Assignees: Shin-Etsu Chemical Co., Ltd., Tokyo (JP); Nippon Telegraph and Telephone Corp., Tokyo (JP)

( * ) Notice: Subject to any disclaimer, the term of this patent is extended or adjusted under 35 U.S.C. 154(b) by 0 days.

(21) Appl. No.: 08/300,245

(22) Filed: Sep. 2, 1994

(30) Foreign Application Priority Data

Sep. 3, 1993 (JP) ................................. 5-244004

(51) Int. Cl.$^7$ ................................. C07C 69/76
(52) U.S. Cl. ................................. 560/57
(58) Field of Search ................................. 560/57

(56) References Cited

U.S. PATENT DOCUMENTS 4,101,323 A    7/1978   Ruhr et al.

FOREIGN PATENT DOCUMENTS

| EP | 0457102 | * | 5/1991 |
| EP | 0457103 | * | 5/1991 |

\* cited by examiner

*Primary Examiner*—Paul J. Killos
(74) *Attorney, Agent, or Firm*—Millen, White, Zelano & Branigan, P.C.

(57) ABSTRACT

Disclosed are novel tert-butyl 4,4-bis(4'-hydroxyphenyl) pentanoate derivatives represented by the following general formula (I);

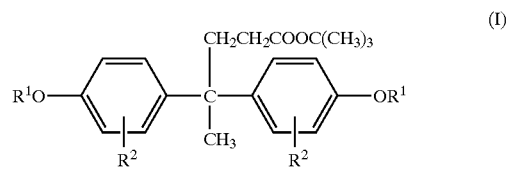

wherein $R^1$ represents a protective group which can be readily eliminated under an acidic condition, and $R^2$ represents a hydrogen atom, a lower alkyl group or a lower alkoxy group: and high energy radiation-responsive positive resist materials using said novel derivatives as dissolution inhibitors.

16 Claims, No Drawings

TERTIARY BUTYL 4,4-BIS(4'-HYDROXYPHENYL) PENTANOATE DERIVATIVES AND POSITIVE RESIST MATERIALS CONTAINING THE SAME

FIELD OF THE INVENTION

The present invention relates to novel dissolution inhibitors and positive resist materials containing said dissolution inhibitors. In particular, it is concerned with tert-butyl 4,4-bis(4'-hydroxyphenyl)pentanoate derivatives which exhibit excellent characteristics when they are used as a dissolution inhibitor in a photoresist, and with positive resist materials which contain said derivatives to be rendered highly sensitive to high energy radiations, such as deep ultraviolet rays (DUV), electron beams and X-rays, developable with an aqueous alkali solution and well suitable for fine processing technology.

BACKGROUND OF THE INVENTION

In proportion as large scale integrated circuits (LSI) are heightened in integration level and operation speed, further fining of the pattern rules is required. However, the light hitherto used in photoexposure technology contained different wavelengths, and these wavelengths were long. Consequently, there was a limit to the finishing of the pattern rules. Thus, attempts were made to use as light source g-line (436 nm) or i-line (365 nm) emitted from an ultrahigh-pressure mercury lamp.

Even in those cases, however, the pattern rule limit was about 0.5 $\mu$m with respect to resolution, and the manufacture of LSI utilizing such photoexposure arts can attain at best the integration level corresponding to 16 Mbit DRAM.

In this context, deep ultraviolet (DUV) lithography using as a light source deep ultraviolet rays, which are shorter in wavelength than g-line and i-line, appears to offer promise as a new processing technology.

DUV lithography can achieve 0.1–0.3 $\mu$m resolutions in the imaging process, and can provide a pattern having effectively vertical walls with respect to the substrate if a resist having a low optical absorbance is used. Moreover, as this technology makes it possible to transfer a pattern in one operation, it offers a higher throughput than electron beam lithography.

In recent years, on the other hand, high intensity KrF excimer laser has been successfully used as the light source for DUV lithography. In order that DUV lithography using such a light source has practical utility in mass production of LSI, it is necessary to use resist materials having low optical absorbance and high sensitivity at the wavelength of that laser.

Thus, there have been lately developed the chemical amplification type resist materials which use an acid as a catalyst and possess not only sensitivities equivalent to or higher than those of conventional high sensitivity resists but also other excellent properties including high resolution and high dry-etching resistance (as proposed, e.g., by Liu et al in *J. Vac. Sci. Technol.*, Vol. B6, p. 379 (1988)). As for the negative resists of the aforementioned type, Shipley Company is already marketing a three-component chemically amplified resist (trade name, SAL601ER7) which consists of a novolak resin, a melamine compound and an acid generator.

When negative resist materials are used in the manufacturing process of LSI, they can serve for wiring and gate forming processes in the LSI production, but it is difficult for them to form contact holes because fine processing techniques are required therein.

On the other hand, hitherto proposed chemically amplified positive resists have a defect such that when they are used without undergoing any modification in forming patterns in accordance with DUV, electron-beam or X-ray lithography the developed patterns tend to overhang in profile because of the lowering of the solubility at the resist surface (K. G. Chiong, et al., J. Vac. Sci. Technol., Vol. B7, (6), p. 1771, (1989)). This overhanging phenomenon is a disadvantage in making the dimensional control of the patterns difficult resulting in impairing dimensional controllability in the processing of substrates by the use of a dry etching technique or, what is worse, in readily causing the collapse of the patterns.

Accordingly, there has been a strong demand for developing positive resist materials of the chemical amplification type which are free from the above-described defect and have high performance.

In compliance with such a demand, Ito et al. have proposed the chemically amplified positive resist material consisting of a resin called PBOCST, or a poly(hydroxystyrene) protected with t-butoxycarbonyl groups, and an onium salt ("Polymers in Electronics", ACS Symposium Series, No. 242, American Chemical Society, Washington D.C., 1984, p. 11).

However, the onium salt used therein contains antimony as a metal component, so that the substrate is contaminated with the antimony. In addition, the resist material recited above suffers from a very great change with the lapse of time after irradiation with DUV or the like.

Another positive resist material for DUV lithography has been proposed by Ueno et al., wherein poly(p-styreneoxytetrahydropyranyl) is used as the principal component and an acid generator is added thereto (36th Ohyo Butsuri Gakkai Kanren Rengo Koenkai, 1989, 1p-k-7).

The foregoing resist material, however, tends to undergo positive to negative inversion when it is exposed to deep ultraviolet rays, electron beams or X-rays.

Moreover, with the two-component positive resist materials as recited above, which are constituted of a resin, whose OH groups are protected with certain groups, and an acid generator, it is necessary to decompose many of the protected groups in order to render the resist soluble in a developer. The decomposition involves a considerably high risk of film thickness variations, in-film stress or air bubbles in the process of LSI production.

Such being the case, there have been developed three-component positive resist materials as chemically amplified positive resist systems which are free from defects of the foregoing two-component ones. The three-component resist system consists of an alkali-soluble resin, a dissolution inhibitor and an acid generator.

As a three-component positive resist material, the resist material RAY/PF (produced by Hoechst AG.), which contains a novolak resin, an acetal compound as a dissolution inhibitor and an acid generator, has been developed for X-ray lithography.

However, the resist sensitivity thereof closely depends on the time elapsed from the exposure to X-rays until the development, because the resist material RAY/PF undergoes chemical amplification at room temperature. Accordingly, it is necessary to systematically perform strict control of that time. In actual practice, however, it is not easy to strictly regulate the time between the exposure and developing steps. That material cannot therefore ensure dimensional stability to the patterns formed therein. In addition, it has another disadvantage in that its optical absorbance at the wavelength of KrF excimer laser beam (248 nm) is so high that it is unsuitable for the lithography using that laser.

In general, in order to effect chemical amplification, many resist materials require a heat treatment after exposure (the so-called post-exposure baking, abbreviated as "PEB"). Although PEB is an additional processing step, compared with the case in which resist systems undergo chemical amplification at room temperature, it enables less severe regulation of the time between exposure and developing steps. Thus, the resist materials requiring PEB can bear stable resist characteristics.

In a resist system which undergoes hydrolysis in the chemical amplification step, water is required for the hydrolysis reaction, and the resist material must therefore contain an appropriate amount of water.

In many cases, however, organic solvents immiscible with water, such as ethoxyethyl acetate, are used as a solvent for coating a resist material on a substrate, and resins which themselves are not compatible with water are used as a constituent of resist materials. Under these circumstances, it is difficult to incorporate a predetermined amount of water in such resist materials, and even if water can be incorporated therein, it will be troublesome to control the water content.

On the other hand, the decomposition reaction of t-butoxycarbonyloxy group does not require any water. More specifically, two components alone, namely, t-butoxycarbonyloxy group and an acid as catalyst, take part in the progress of the reaction. Therefore, the decomposition reaction is more suitable for chemical amplification.

Moreover, many of the t-butoxycarbonyloxy containing compounds are known to inhibit the dissolution of novolak resins, which infers that t-butoxycarbonyloxy group has dissolution inhibiting effect on novolak resins.

Taking into account the knowledge described above, Schlegel et al. have reported a three-component positive resist material consisting of a novolak resin, t-butoxycarbonyl protected bisphenol A as dissolution inhibitor and pyrogallol methanesulfonic acid ester (37th Ohyo Butsuri Gakkai Kanren Rengo Koenkai, Spring 1990, 28p-ZE-4).

Such a resist material is, however, difficult to use practically because the novolak resin has high optical absorbance.

Schwalm et al. have developed bis(p-t-butoxycarbonyloxyphenyl)iodonium hexafluoroantimonate as a compound in which the two functions of the dissolution inhibitor and the acid generator are combined (Polymer for Microelectronics, Tokyo 1989, Session A38), and have reported the mixture of that compound with a novolak resin as a positive resist material for DUV lithography.

However, as the foregoing resist material contains not only the novolak resin having high optical absorbance but also the metal, it is not suitable for practical application.

On the other hand, it is known that in the chemically amplified positive resist materials of three-component type, which are constituted of a resin, a dissolution inhibitor and an acid generator, the dissolution inhibitor has a particularly great influence on the performance of the resist material through its ability to control the dissolution speed of a resist film in an alkaline developer (that is to say, to increase the ratio of a dissolution speed of the area irradiated with high energy beams to the issolution speed of the unirradiated area, which is abbreviated as "dissolution speed ratio", hereinafter). More specifically, the efficiency in forming resist patterns is greatly heightened by adding to a resist material a compound capable of making the high energy beams (e.g., ultraviolet rays) irradiated area of a resist film highly soluble in an alkaline developer (namely, a dissolution inhibitor).

As for the dissolution inhibitor which has, as described above, a great influence upon the performance of a photoresist, di-t-butoxycarbonyl-protected bisphenol A represented by the following formula (a), di-t-butoxycarbonyl-protected bisphenol F represented by the following formula (b), 4-t-butoxycarbonylbiphenyl represented by the following formula (c), deoxycholic acid t-butyl ester represented by the following formula (d) and cholic acid t-butyl ester represented by the following formula (e) are well-known examples thereof.

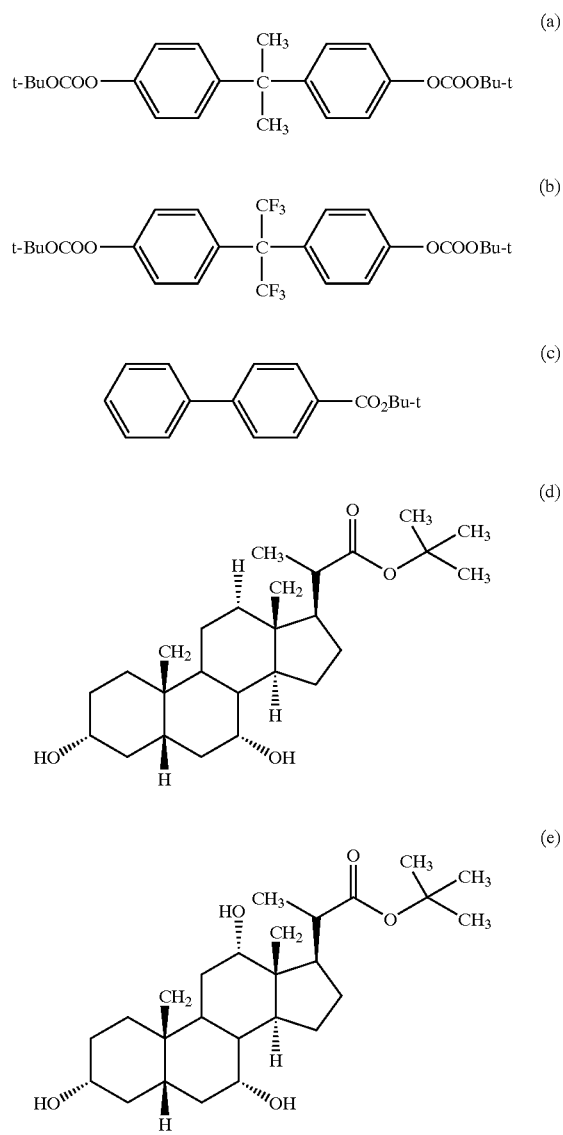

In the above formulae, t-Bu or Bu-t stands for a t-butyl group.

All of those dissolution inhibitors, however, have defects such that they cannot bring sufficient dissolution contrast between the exposed area and the unexposed area of a resist, thereby failing in conferring satisfactory resolution and sensitivity on the resist, and causing a change in shape of the resist pattern with the lapse of time.

More specifically, di-t-butoxycarbonyl-protected bisphenol A and di-t-butoxycarbonyl-protected bisphenol F have small dissolution speed ratios and are limited in amount to be added because of their low compatibilities with resins, although they have great inhibiting effect upon dissolution of resins, have small ultraviolet absorptivity and are available at low prices.

4-t-Butoxycarbonylbiphenyl, although it has a relatively great dissolution speed ratio and great ultraviolet absorptivity, hinders the control of light permeability into a resist film.

Cholic acid t-butyl ester and chenodeoxycholic acid t-butyl ester, on the other hand, can function as excellent dissolution inhibitors since they have not only small ultraviolet absorptivity but also good compatibility with novolak resins. However, they cannot exhibit sufficient inhibiting effect upon dissolution of poly(hydroxystyrene)s, and so they cause the so-called film-thinning phenomenon, or a phenomenon such that the unirradiated part of a resist film dissolves in an alkaline developer. In addition, those compounds cannot be supplied constantly because the raw material thereof is a natural product.

Therefore, we have made intensive studies on dissolution inhibitors for photoresists. As a result, we have found out that novel derivatives of t-butyl 4,4-bis(4'-hydroxyphenyl) pentanoates can effectively function as dissolution inhibitors for photoresists, and when they are used as dissolution inhibitors for poly(hydroxystyrene) resins the problems encountered with conventional chemically amplified positive resist materials for high energy radiation lithography can be solved and not only higher performance than ever with respect to sensitivity, resolution and process suitability but also excellent preservation stability can be realized in positive resist materials for high energy radiation lithography, thereby achieving the present invention.

SUMMARY OF THE INVENTION

Thus, a first object of the present invention is to provide novel derivatives of t-butyl 4,4-bis(4'-hydroxyphenyl) pentanoates which are effective as dissolution inhibitors for photoresists.

A second object of the present invention is to provide positive resist materials for high energy radiation lithography which have not only higher performance than ever with respect to sensitivity, resolution and process suitability but also excellent preservation stability.

The above-described objects are respectively attained with t-butyl 4,4-bis(4'-hydroxyphenyl)pentanoate derivatives represented by the following general formula (I), and positive resist materials which are constituted of three components, (a) a poly(hydroxystyrene) resin in which hydrogen atoms of the hydroxy groups are partly replaced by t-butoxycarbonyl groups, (b) a dissolution inhibitor and (c) an acid generator, with the three components (a), (b) and (c) having the weight proportions defined by the relations: $0.55 \leq a$, $0.07 \leq b \leq 0.40$, $0.005 \leq c \leq 0.15$, and $a+b+c = 1$, and are developable with an aqueous alkali solution and responsive to high energy radiation; said dissolution inhibitor (b) being a compound selected from the t-butyl 4,4-bis(4'-hydroxyphenyl)pentanoate derivatives represented by general formula (I):

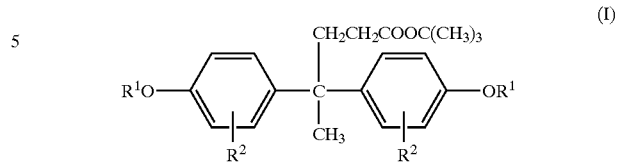

wherein $R^1$ represents a protective group which can be readily eliminated under an acidic condition, and $R^2$ represents a hydrogen atom, a lower alkyl group or a lower alkoxy group.

DETAILED DESCRIPTION OF THE INVENTION

Specific examples of $R^1$ in the above formula (I) include a t-butoxycarbonyl group, a t-butoxycarbonylmethyl group, a tetrahydropyranyl group, a methoxymethyl group, a diphenylmethyl group, a triphenylmethyl group, a trimethylsilyl group, a triethylsilyl group and a t-butyldimethylsilyl group. Suitable examples of $R^2$, on the other hand, include a hydrogen atom, a methyl group, an ethyl group, a methoxy group and an ethoxy group.

The t-butyl 4,4-bis(4'-hydroxyphenyl)pentanoate derivatives having general formula (I) illustrated above can be obtained by introducing protective groups represented by $R^1$ into the phenolic hydroxy groups of t-butyl 4,4-bis(4'-hydroxyphenyl)pentanoates represented by the following general formula (II). When the phenolic hydroxy groups in general formula (II) are protected by groups other than $R^1$, the protective groups are first eliminated to convert the protected t-butyl esters into the t-butyl esters of general formula (II), and then $R^1$s are introduced therein.

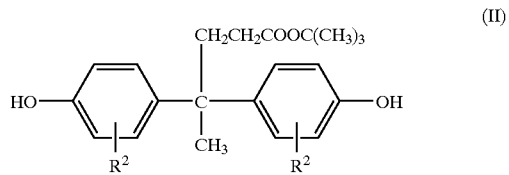

In introducing protective groups $R^1$ into a t-butyl ester of general formula (II), there is no particular restriction as to the species of the compound used therefor. For instance, dicarbonic acid di-t-butyl ester, dihydro-2H-pyran, t-butyldimethylchlorosilane, methoxymethyl chloride and so on can be used for the introduction of protective groups.

Therein, it is desirable that a compound as cited above be used in an amount of from 2 to 5 moles per mole of the t-butyl ester of formula (II).

In this introduction reaction, it is possible to use a catalyst such as a paratoluenesulfonate (e.g., pyridinium paratoluenesulfonate), imidazole, etc., if needed.

Further, pyridine, methylene chloride, N,N-dimethylformamide and so on can be used therein as a solvent.

Additionally, a synthesis method for a t-butyl 4,4-bis(4'-hydroxyphenyl)pentanoate represented by general formula (II) is disclosed in European Patent No. 457102.

According to that method, the 4,4-bis(4'-hydroxyphenyl) pentanoic acid is made to react with isobutylene in the presence of isopropylmethyl ethyl ketone as a solvent and sulfuric acid as a catalyst. Thus, the main products obtained are compounds into which plural numbers of t-butyl groups are introduced. Therefore, it is difficult to obtain the t-butyl ester of general formula (II) in a highly pure state.

In contrast to the above-cited method, the present invention has succeeded in obtaining highly pure t-butyl 4,4-bis(4'-hydroxyphenyl)pentanoates having general formula (II) or the phenolic OH-protected compounds thereof. The method adopted in the present invention consists in firstly treating a 4,4-bis(4'-hydroxyphenyl)pentanoic acid or the phenolic OH-protected compound thereof with trifluoroacetic acid anhydride, and then reacting with t-butyl alcohol.

In the treatment described above, it is preferable for trifluoroacetic acid anhydride to be used in an amount of from 3 to 5 moles per mole of the 4,4-bis(4'-hydroxyphenyl) pentanoic acid.

In the reaction described above, it is preferable for t-butyl alcohol to be used in an amount of from 3 to 5 moles per mole of the 4,4-bis(4'-hydroxyphenyl)pentanoic acid.

In both the treatment and the reaction, there can be used a solvent such as tetrahydrofuran, methylene chloride, chloroform, ethyl ether, etc.

In the treatment with trifluoroacetic acid anhydride, it is desirable that the treatment temperature be in the range of $-10°$ C. to $10°$ C. and the treatment time in the range of 0.5 to 3 hours.

In the reaction with t-butyl alcohol, it is desirable that the reaction temperature be in the range of $-10°$ C. to $10°$ C. and the reaction time in the range of 0.5 to 18 hours.

At the conclusion of the reaction, the reaction solution obtained is neutralized, if needed, and the product is extracted with chloroform or the like. The extracted product is purified in a conventional manner to give a highly pure t-butyl 4,4-bis(4'-hydroxyphenyl)pentanoate represented by general formula (II).

By the use of the thus produced t-butyl 4,4-bis(4'-hydroxyphenyl)pentanoates as starting material, it becomes possible to obtain the t-butyl 4,4-bis(4'-hydroxyphenyl) pentanoate derivatives of general formula (I) in a highly pure state.

Thus, the novel t-butyl 4,4-bis(4'-hydroxyphenyl) pentanoate derivatives obtained in the present invention can fully achieve their effect as the dissolution inhibitor of three-component chemically amplified resists.

Next the positive resist materials containing the t-butyl 4,4-bis(4'-hydroxyphenyl)pentanoate derivatives of the present invention are described below in detail.

The resin used as the component (a) in the present invention is a poly(hydroxystyrene) resin in which hydrogen atoms of the hydroxy groups are partly replaced by t-butoxycarbonyl groups. In this poly(hydroxystyrene) resin, it is desirable that the introduction rate of t-butoxycarbonyl groups be in the range of 10 to 50%. When the introduction rate is not lower than 50%, the solubility of the resin in an aqueous alkali solution is lowered. Therefore, the resulting resist material has lowered sensitivity when developed with a conventional developer. When the introduction rate is below 10%, on the other hand, the resulting resin can have insufficient dissolution-inhibiting effect.

The replacement of the hydrogen atoms in hydroxy groups with t-butoxycarbonyl groups can be effected by a method for protecting functional groups, which is often used in peptide synthesis. Specifically, the protection can be simply performed by reacting a poly(hydroxystyrene) with di-t-butyl dicarbonate in the pyridine solution thereof.

It is desirable that the poly(hydroxystyrene) resin have a weight average molecular weight of at least 10,000 from the viewpoint of the heat resistance of the resist film formed and, what is more, be a monodisperse system with respect to molecular weight distribution from the standpoint of the precision of the pattern formed.

However, when there is used a poly(hydroxystyrene) resin having a broad distribution of molecular weight, such as those prepared by radical polymerization, the resulting resist material involves high molecular weight species which are hard to dissolve in an aqueous alkali solution. These species are responsible for the formed pattern's sloping at the base. To form a high precision pattern, it is therefore advantageous to use a monodisperse poly(hydroxystyrene) resin as prepared by living polymerization.

In accordance with the present invention, a resist material using a poly(hydroxystyrene) obtained by living polymerization (e.g., one which has a molecular weight of 10,000 and a molecular weight distribution of 1.1) can form a 0.2 $\mu$m line and space pattern with no sloping at the base and with high precision. Moreover, the formed pattern has satisfactory heat resistance, because no deformation is caused therein by 10 minutes' baking at $150°$ C.

On the other hand, the pattern formed using a poly(hydroxystyrene) prepared by radical polymerization (e.g., one which has an average molecular weight of 12,000 and a molecular weight distribution of 3.0) has heat resistance almost equivalent to the above-described case. However, the sloping at the base is observed even on a 0.5 $\mu$m line and space pattern. With this poly(hydroxystyrene), therefore, it is hardly possible to achieve the resolution of 0.2 $\mu$m.

Additionally, the term "a monodisperse polymer" as used herein means a polymer which is a monodisperse system in terms of its molecular weight distribution, that is, $1.05 \leq Mw/Mn \leq 1.50$. Herein, Mw stands for the weight average molecular weight of a polymer, and Mn the number average molecular weight.

As for the polymer prepared by living polymerization, its weight average molecular weight can easily be calculated from the weight of the monomer used and the mole number of the polymerization initiator used, or can be determined by a light scattering method. The number average molecular weight thereof can easily be measured with a membrane osmometer.

Further, the molecular weight distribution can be evaluated by Gel Permeation Chromatography (GPC), and the molecular structure can easily be ascertained with the infrared absorption (IR) or $^1$H-NMR spectrum.

A monodisperse resin (or polymer) can be obtained (1) through the fractionation treatment of a product prepared using a radical polymerization method, which thus has a broad molecular weight distribution, or (2) by adopting a living polymerization method. However, the living polymerization method is preferred because the process for rendering the product monodisperse is simple.

Thus, the synthesis of a monodisperse poly(hydroxystyrene) resin according to a living polymerization method is illustrated below in detail taking the case of poly(p-hydroxystyrene).

Even if it is attempted to make p-hydroxystyrene monomer undergo living polymerization as it is, the polymerization cannot occur because the hydroxyl group of the monomer reacts with a polymerization initiator. Therefore, there is adopted a method such that a hydroxy-protecting group is introduced into the monomer, the resulting monomer is subjected to living polymerization and then the protecting group is removed from the polymerization product. Thus, the desired p-hydroxystyrene polymer is obtained.

Specific examples of such a protecting group include t-butyl, dimethylphenylcarbinyldimethylsilyl, t-butoxycarbonyl, tetrahydropyranyl and t-butyldimethylsilyl groups. In particular, t-butoxycarbonyl group is preferred over the others.

In the aforementioned living polymerization, it is desirable that an organometallic compound be used as polymerization initiator.

Suitable examples of such an organometallic compound include organic alkali metal compounds such as n-butyl lithium, sec-butyl lithium, tert-butyl lithium, sodium naphthalene, sodium anthracene, disodium α-methylstyrene tetramer, cumyl potassium and cumyl cesium.

It is preferable for the living anion polymerization to be carried out in an organic solvent. This organic solvent can be an aromatic hydrocarbon, a cyclic ether or an aliphatic hydrocarbon, with specific examples including benzene, toluene, tetrahydrofuran, dioxane, tetrahydropyran, dimethoxyethane, n-hexane and cyclohexane.

These organic solvents may be used alone or as a mixture of two or more thereof. In particular, it is advantageous to use tetrahydrofuran as the solvent.

The suitable concentration of a monomer in the polymerization reaction is in the range of 1 to 50 wt %, particularly 1 to 30 wt %. The reaction is performed with stirring under high vacuum or in an atmosphere of inert gas such as argon or nitrogen.

The reaction temperature can be chosen freely in a range extending from −100° C. to the boiling point of the organic solvent used. However, it is advantageous to choose the reaction temperature from the range of −78° C. to 0° C. when tetrahydrofuran is used as solvent, while room temperature is preferred as the reaction temperature when benzene is used as solvent.

By the reaction of about 10 minutes' to about 7 hours' duration under a condition as described above, only the vinyl group takes part in the polymerization reaction to produce a desired polymer.

At the point that the desired degree of polymerization has been attained, the polymerization reaction is terminated by adding a terminator such as methanol, water or methyl bromide to the reaction system, thereby obtaining a living polymer having the desired molecular weight.

Further, an appropriate solvent is added to the reaction mixture obtained to yield a precipitate. The precipitate is washed and dried, thereby purifying and isolating the intended living polymer.

In the living polymerization, 100% of monomer molecules take part in the reaction, so that the yield rate of the polymer produced is approximately 100%. Such being the case, the molecular weight of the living polymer can be adjusted to a desired one by properly controlling the amount of the monomer used and the mole number of the reaction initiator.

The molecular weight distribution of the thus obtained living polymer is monodisperse ($1.05 \leq Mw/Mn \leq 1.50$).

Further, dimethylphenylcarbyldimethylsilyl or t-butyl groups as the protecting groups are removed to obtain poly(p-hydroxystyrene).

The removal of the protecting groups can easily be achieved by dissolving the obtained living polymer in a solvent such as dioxane, acetone, acetonitrile, benzene or a mixture of two or more thereof, and then by adding dropwise an acid such as hydrochloric acid, hydrobromic acid, pyridinium paratoluenesulfonate, etc.

In the above-described removal reaction, neither the cleavage of the main chain of the polymer nor the intermolecular cross-linking reaction occurs. Accordingly, the poly (p-hydroxystyrene) obtained is still a monodisperse system.

The dissolution inhibitor used as the present component (b) is a material of the kind which can have solubility in an aqueous alkali solution when the resist film is irradiated with high energy beams, such as deep ultraviolet rays, subjected to a thermal treatment, if needed, and then developed with an alkali developer. To the material of such a kind are applied the present novel t-butyl 4,4-bis(4'-hydroxyphenyl) pentanoate derivatives represented by general formula (I).

The content of the dissolution inhibitor in the present resist material is desirably in the range of 7 to 40 wt %. When the content is less than 7 wt %, the dissolution inhibiting effect is small; while when it is greater than 40 wt %, the mechanical strength and heat resistance of the resist film decline.

Acid generators which can be used in the present invention are materials capable of decomposing upon irradiation with high energy beams to produce acids. Such materials include various types of compounds, and onium salts such as sulfonium salts, iodonium salts and so on can be suitable examples thereof. As for the onium salts, $(C_6H_5)_2I^{+-}X$, $(C_6H_5)_3S^{+-}X$, $(C_6H_5SC_6H_4)(C_6H_5)_2S^{+-}X$, $(CH_3OC_5H_4)(C_6H_5)_2I^{+-}X$, $[(CH_3)_3C-C_6H_5]_2I^{+-}X$ and the like are specific examples thereof. These onium salts may be used alone or as a mixture of two or more thereof.

In the above formulae, X represents a p-toluenesulfonyl group, trifluoromethanesulfonyl group, hexafluoroantimonate group, hexafluorophosphate group, tetrafluoroborate group or so on.

Compounds other than onium salts can also be used as acid generators in the present invention, independently or as mixtures with onium salts.

Specific examples of such compounds include diazo compounds such as di(phenylsulfonyl)diazomethane, etc., benzyl tosylates such as 2,6-dinitrobenzyl tosylate, etc., benzoin tosylate and triazine derivatives.

The content of an acid generator in the present resist material is preferably in the range of 0.5 to 15 wt %. When the content is less than 0.5 wt %, the resist material cannot have improved sensitivity; while the contents greater than 15 wt % cause not only an increase in production cost of the resist material but also a decrease in mechanical strength of the resist film.

Forming patterns on a substrate using the present resist materials can be performed with ease in the following manner:

A solution of the present resist material is spin-coated on a substrate, and then prebaked to prepare a coated substrate. The coated substrate is irradiated with high energy beams. Therein, the acid generator in the coating is decomposed to produce an acid. Then, a thermal treatment is performed, and thereby is caused the decomposition of the t-butoxycarbonyloxy groups as the produced acid acts as a catalyst. The decomposed groups have no longer the resist dissolution inhibiting effect. As a result of it, a latent image is formed on the substrate. The substrate having the latent image thereon is then developed with an aqueous alkali solution, and rinsed with water to provide a positive pattern.

A reason why the present resist materials have high sensitivities to high-energy beams and high resolution is not necessarily clear. However, it can be assumed that the t-butyl 4,4-bis(4'-hydroxyphenyl)pentanoate derivatives used as dissolution inhibitor in the present invention can increase the dissolution speed ratio since they have not only great dissolution inhibiting power but also satisfactory compatibilities with phenolic resins including poly(hydroxystyrene)s.

In accordance with embodiments of the present invention, the present t-butyl 4,4-bis(4'-hydroxyphenyl)pentanoate derivatives can fulfil their excellent functions as dissolution inhibitor in chemically amplified resists of three-component type. The resists using these derivatives can ensure high resolution in the resist images.

Further, the present positive resist materials have high sensitivity to high energy radiation, particularly to deep ultraviolet rays with shorter wavelengths (e.g., KrF excimer laser).

Moreover, not only is their plasma etching resistance is high and the resist patterns formed therein have excellent heat-resisting property, but also their absorbance is small in the deep ultraviolet region described above. Therefore, the present resist materials are well suited for fine processing of the substrates used for LSI and the like. In addition, the positive resist materials of the present invention. contain no metallic elements, have resist characteristics slightly depending on the time lapsed after irradiation, and require no water in the chemical amplification process. In these respects also, the present resist materials are extremely suitable for the fine processing of substrates for LSI and the like by high energy-radiation lithography.

EXAMPLES

The present invention will now be described in greater detail by reference to the following examples, but it will be understood that the invention is not to be construed as being limited by these examples in any way.

Additionally, the synthesis of a t-butyl 4,4-bis(4'-hydroxyphenyl)pentanoate, which is a starting material for obtaining the present derivatives, is illustrated prior to the Examples.

Synthesis Example 1

4,4-Bis(4'-hydroxyphenyl)pentanoic acid in an amount of 57.3 g (0.20 mole) was dissolved in 200 ml of tetrahydrofuran. The resulting solution was stirred under an atmosphere of nitrogen and cooled to 5° C. with an ice-water bath. Thereto, 138 g (0.657 mole) of trifluoroacetic acid anhydride was added dropwise over a 30-minute period.

After the addition, the stirring was continued for an additional two hours at room temperature, and then the resulting solution was cooled to 5° C. with an ice-water bath. Then, 150 ml of t-butyl alcohol was dripped into the solution over a period of about 10 minutes. After the conclusion of the dripping, the reaction mixture was stirred for 6 hours at room temperature.

The resulting solution was cooled to 5° C. with an ice-water bath, and thereinto was dripped 150 ml of concentrated aqueous ammonia. Thereafter, the reaction solution was allowed to stand for one night. From the resulting solution, the product was extracted with chloroform.

The extract obtained was dried with anhydrous sodium sulfate, and the solvent was distilled away therefrom. Thus, a semicrystalline residue was obtained.

The residue obtained was admixed with n-hexane, stirred and then filtrated. Thus, the intended product was obtained in a yield of 48.7 g (0.142 mole; 71.1%).

The product obtained was ascertained to be t-butyl 4,4-bis(4'-hydroxyphenyl)pentanoate having the following formula (i) by the NMR spectral analysis shown below:

NMR (CDCL$_3$, δ); 1.41 (9H, s), 1.75 (3H, s), 1.89 (2H, t), 2.18 (2H, t), 3.87 (2H, s), 6.60 (4H, d), 6.89 (4H, d).

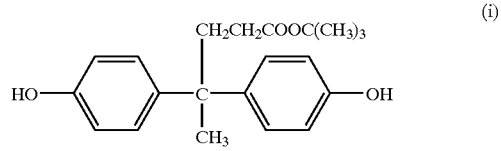

(i)

Example 1

The t-butyl 4,4-bis(4'-hydroxyphenyl)pentanoate obtained in Synthesis Example 1 in an amount of 2.94 g (10 mmole) was dissolved in 50 ml of pyridine, admixed with 4.8 g (22 mmole) of di-t-butyl dicarbonate, and stirred at 40° C. for 30 hours to complete the reaction.

From the resulting solution, the solvent was distilled away under reduced pressure. The thus obtained residue was recrystallized from water-containing methanol to give 3.56 g of colorless crystals having a melting point of 107° C. (yield: 72%).

The product thus obtained was ascertained to be t-butyl 4,4-bis(4'-t-butoxycarbonyloxyphenyl)pentanoate represented by the following formula (ii), by the NMR spectral analysis shown below:

NMR (CDCL$_3$, δ); 1.40 (9H, s), 1.54 (18H, s), 1.58 (3H, s), 2.00 (2H, t), 2.36 (2H, t), 7.06 (4H, d), 7.17 (4H, d).

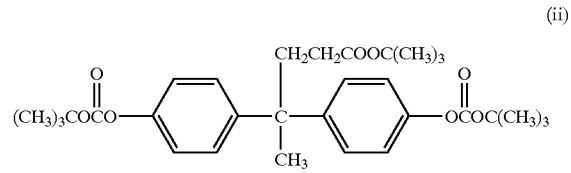

(ii)

Example 2

The t-butyl 4,4-bis(4'-hydroxyphenyl)pentanoate obtained in Synthesis Example 1 in an amount of 2.94 g (10 mmole) was dissolved in 20 ml of N,N-dimethylformamide, admixed with 2.76 g of potassium carbonate and 3.9 g (20 mmole) of t-butyl bromoacetate, and stirred at 60° C. for 6 hours to complete the reaction.

After the resulting solution was allowed to cool down, it was dissolved in 50 ml of chloroform, and then washed with 50 ml each of purified water three times. The organic layer was dried with anhydrous sodium sulfate, and the solvent was removed therefrom by distillation. The light brown oily residue thus obtained was chromatographed with silica gel to isolate 4.31 g of the intended product. The yield of the product was 75.5%.

The product obtained was ascertained to be the t-butyl pentanoate derivative represented by the formula (iii) illustrated below by the NMR spectral analysis shown below:

NMR (CDCL$_3$, δ); 1.39 (9H, s), 1.47 (18H, s), 1.58 (3H, s), 1.98 (2H, t), 2.32 (2H, t), 4.47 (4H, s), 6.78 (4H, s), 7.07 (4H, s).

(iii)

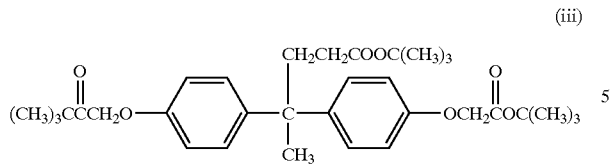

(v)

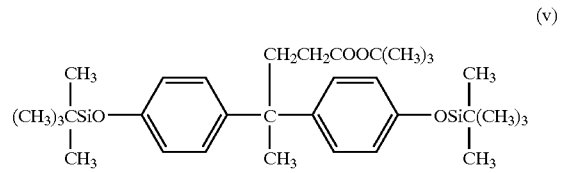

Example 3

The t-butyl 4,4-bis(4'-hydroxyphenyl)pentanoate obtained in Synthesis Example 1 in an amount of 2.94 g (10 mmole) was dissolved in 100 ml of methylene chloride, admixed first with 0.25 g (1 mmole) of pyridinium para-toluenesulfonate and then with 2.52 g (30 mmole) of 3,4-dihydro-2H-pyran. The resulting mixture was stirred at room temperature (20° C.) for 3 hours to complete the reaction.

After washing the resulting solution with water, it was dried with anhydrous sodium sulfate, followed by removal of the solvent through distillation. Thus, a glassy residue was obtained. From this residue, 4.02 g of the intended product was isolated by silica gel chromatography. The yield of the product was 82%.

The product thus obtained was ascertained to be t-butyl 4,4-bis[p-(tetrahydropyran-2'-yl)oxyphenyl]pentanoate represented by the following formula (iv), by the NMR spectral analysis shown below:

NMR (CDCL$_3$, δ); 1.42 (9H, s), 2.13 (2H, m), 2.38 (2H, m), 3.59 (6H, m), 3.87 (6H, m), 5.35 (4H, s), 5.91 (2H, s), 6.93 (4H, d), 7.08 (4H, d)

(iv)

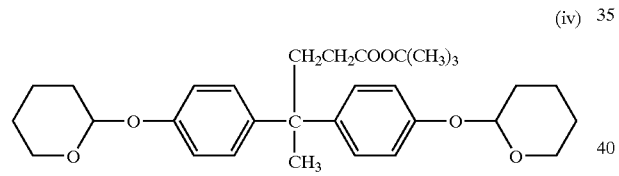

Example 4

The t-butyl 4,4-bis(4'-hydroxyphenyl)pentanoate obtained in Synthesis Example 1 in an amount of 2.94 g (10 mmole) was dissolved in 30 ml of N,N-dimethylformamide, and admixed with 0.68 g (1 mmole) of imidazole. Thereto was added 3.32 g (22 mmole) of t-butyldimethylchlorosilane. The resulting mixture was stirred at room temperature for 4 hours to complete the reaction.

The reaction solution obtained was dissolved in chloroform, and then washed with water. The organic layer was dried with anhydrous sodium sulfate, followed by removal of the solvent through distillation.

From the residue thus obtained, 4.21 g of the intended product was isolated by silica gel chromatography. The yield of the product was 81%.

This product was ascertained to be t-butyl 4,4-bis(4'-t-butyldimethylsilyloxyphenyl)pentanoate represented by the following formula (v), by the NMR spectral analysis shown below:

NMR (CDCL$_3$, δ); 0.24 (12H, s), 0.88 (18H, s), 1.42 (9H, s), 1.55 (3H, s), 2.10 (2H, m), 2.34 (2H, m), 6.93 (4H, d), 7.08 (4H, d)

Example 5

The t-butyl 4,4-bis(4'-hydroxyphenyl)pentanoate obtained in Synthesis Example 1 in an amount of 2.94 g (10 mmole) was dissolved in 100 ml of methylene chloride, admixed first with 3.1 ml (22 mmole) of triethylamine and then with 3.54 g (22 mmole) of methoxymethyl chloride. The resulting mixture was stirred at room temperature for 12 hours to complete the reaction.

The resulting solution was washed with 100 ml each of water three times, and the organic layer was dried with anhydrous sodium sulfate, followed by removal of the solvent through distillation. Thus, an oily residue was obtained. From this residue, 2.86 g of the intended product was isolated by silica gel chromatography. The yield of the product was 75%.

The product thus obtained was ascertained to be t-butyl 4,4-bis(4'-methoxymethyloxyphenyl)pentanoate represented by the following formula (vi), by the NMR spectral analysis shown below:

NMR (CDCL$_3$, δ); 1.58 (3H, s), 2.00 (2H, t), 2.34 (2H, t), 3.51 (6H, s), 5.20 (4H, s), 7.06 (4H, d), 7.17 (4H, d)

(vi)

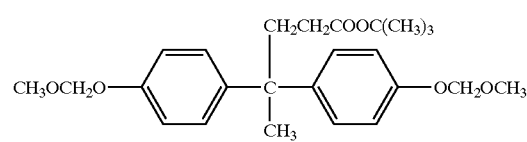

Example 6

A resist solution containing the following ingredients:

| | |
|---|---|
| Base resin | 81 parts by weight |
| t-Butyl 4,4-bis(4'-t-butoxycarbonyloxyphenyl) pentanoate(Dissolution inhibitor obtained in Example 1) | 14 parts by weight |
| Phenyldi(4-t-butoxyphenyl)sulfonium trifluoromethane-sulfonate (Acid generator) | 5 parts by weight |
| Ethoxyethyl acetate | 400 parts by weight | was spin-coated onto a silicon substrate at 2,000 rpm, and prebaked on a hot plate at 85° C. for 1 minute. Thus, there was obtained the resist-coated substrate having a resist film thickness of 0.7 μm.

The base resin used herein was a poly(p-hydroxystyrene) resin having a t-butoxycarbonyl group-introduction degree of 20 mole %, a molecular weight of 10,000 and a molecular weight distribution (Mw/Mn) of 1.05.

After imaging on the coating side of the resist-coated substrate with KrF excimer laser (wavelength: 248 nm), the resist coating was subjected to a heat treatment at 85° C. for 2 minutes. The resulting coating was developed with a 2.4 wt % aqueous solution of tetramethylamonium hydroxide (TMAH) for 1 minute, and then rinsed with water for 30 seconds, thereby forming a pattern on the silicon substrate (patterned substrate).

The thus formed pattern on the substrate showed positive-tone characteristics, and the $D_o$ sensitivity of the resist film was 35 mJ/cm².

When an electron beam having an accelerating voltage of 30 kV was used instead of the foregoing KrF excimer laser, on the other hand, the $D_o$ sensitivity of the resist film was 13.3 µC/cm².

Each of the line-and-space pattern and the hole pattern formed with KrF excimer laser had the resolution of 0.25 µm, and the patterns formed had almost vertical side walls; while the resolution of 0.2µm was achieved when the electron beam was used for imaging.

Example 7

In accordance with the procedures adopted in Example 6, a patterned substrate was produced using a resist solution prepared in the same manner as in Example 6, except that t-butyl 4,4-bis(4'-t-butoxycarbonylmethoxyphenyl)pentanoate (prepared in Example 2) was used as dissolution inhibitor in place of t-butyl 4,4-bis(4'-t-butoxycarbonyloxyphenyl)pentanoate, and examined for $D_o$ sensitivity and resolution.

The thus evaluated $D_o$ sensitivity of the resist film in imaging with KrF excimer laser was 47 mJ/cm².

In the case where the electron beam having an accelerating voltage of 30 kV was used for imaging instead of KrF excimer laser, the $D_o$ sensitivity of the resist film was 21.6 µC/cm².

Additionally, the pattern formed herein had resolution equivalent to that achieved in Example 6.

Examples 8 to 21

In accordance with the procedures adopted in Example 6, patterned substrates were produced respectively using resist solutions prepared in the same manner as in Example 6, except that the acid generators set forth in Table 1 were used respectively in place of phenyldi(4-t-butoxytriphenylsulfonium triflate (the term "triflate" stands for trifluoromethanesulfonate, hereinafter), and examined for $D_o$ sensitivity and resolution. The thus evaluated $D_o$ sensitivities are shown in Table 2.

Additionally, the patterns formed herein were slightly different from one another, but a 0.3 µm line-and-space pattern was resolved in every patterned substrate.

TABLE 1

| Acid Generators used | Symbol |
| --- | --- |
| 4-Methoxyphenyldiphenylsulfonium triflate | PAG 1 |
| 4-Methoxyphenyldiphenylsulfonium hexafluoroantimonate | PAG 2 |
| 4-Fluorophenyldiphenylsulfonium triflate | PAG 3 |
| 4-Fluorophenyldiphenylsulfonium tosylate | PAG 4 |
| 4-Phenylthiophenyldiphenylsulfonium triflate | PAG 5 |
| Di(4-t-butoxycarbonyloxyphenyl)phenylsulfonium triflate | PAG 6 |
| 4-Methoxyphenyliodonium triflate | PAG 7 |
| 4-Methoxyphenyliodonium tosylate | PAG 8 |
| Di(4-t-butylphenyl)iodonium triflate | PAG 9 |
| 4-Trifluoromethylphenyldiphenylsulfonium triflate | PAG 10 |
| Benzoin tosylate | PAG 11 |
| Pyrogallol trimesylate | PAG 12 |
| 2,5-Dinitrobenzyl tosylate | PAG 13 |
| Di(4-t-butylphenylsulfonyl)diazomethane | PAG 14 |

TABLE 2

| Resist Sample | Acid Generator (represented by Symbol in Table 1) | KrF Sensitivity $D_o$(mJ/cm²) |
| --- | --- | --- |
| Example 8 | PAG 1 | 55 |
| Example 9 | PAG 2 | 21 |
| Example 10 | PAG 3 | 30 |
| Example 11 | PAG 4 | 46 |
| Example 12 | PAG 5 | 72 |
| Example 13 | PAG 6 | 15 |
| Example 14 | PAG 7 | 35 |
| Example 15 | PAG 8 | 29 |
| Example 16 | PAG 9 | 41 |
| Example 17 | PAG 10 | 23 |
| Example 18 | PAG 11 | 94 |
| Example 19 | PAG 12 | 123 |
| Example 20 | PAG 13 | 29 |
| Example 21 | PAG 14 | 66 |

Examples 22 to 32

In accordance with the same process as adopted in Example 6, patterned substrates were produced respectively using resist solutions prepared in the same manner as in Example 6, except that the base resins set forth in Table 3 were used respectively in place of the base resin used in Example 6, the dissolution inhibitors set forth in Table 4 were used respectively in place of the dissolution inhibitor used in Example 6 and 4-phenylthiophenyldiphenylsulfonium triflate (PAG 5) was used as acid generator in place of phenyldi(4-t-butoxyphenyl)sulfonium triflate. The patterned substrates thus obtained were each examined for $D_o$ sensitivity and resolution by the same methods as in Example 6. The thus evaluated $D_o$ sensitivities are shown in Table 5.

Additionally, the resolutions achieved herein were a little bit different from one another, but a 0.3 µm line-and-space pattern was resolved in each of the patterned substrates.

TABLE 3

| Base Resin | Mw | Mw/Mn | Symbol |
| --- | --- | --- | --- |
| Poly(hydroxystyrene) | 15,000 | 1.10 | RESIN 1 |
| Poly(hydroxystyrene) whose OH groups are replaced with t-butoxycarbonyloxy groups in a proportion of 30 mole % | 13,000 | 1.13 | RESIN 2 |
| Poly(hydroxystyrene) whose OH groups are replaced with t-butoxycarbonyloxy groups in a proportion of 40 mole % | 50,000 | 1.11 | RESIN 3 |
| Poly(hydroxystyrene) whose OH groups are replaced with tetrahydropyranyloxy groups in a proportion of 25 mole % | 20,000 | 1.00 | RESIN 4 |
| Styrene-hydroxystyrene copolymer (styrene fraction: 20 mole %) | 10,000 | 1.31 | RESIN 5 |

TABLE 4

| Dissolution Inhibitor | Symbol |
| --- | --- |
| t-Butyl 4,4-bis(4'-t-butoxycarbonyloxyphenyl)-pentanoate | DRI 1 |
| t-Butyl 4,4-bis(4'-t-butoxycarbonylmethoxyphenyl)-pentanoate | DRI 2 |
| t-Butyl 4,4-bis[p-(tetrahydropyran-2'-yl)oxyphenyl]-pentanoate | DRI 3 |

TABLE 4-continued

| Dissolution Inhibitor | Symbol |
|---|---|
| t-Butyl 4,4-bis(4'-t-butyldiethylsilyloxyphenyl)-pentanoate | DRI 4 |
| t-Butyl 4,4-bis(4'-methoxymethyloxyphenyl)pentanoate | DRI 5 |

TABLE 5

| Resist Sample | Base Resin (represented by Symbol in Table 3) | Dissolution Inhibitor (represented by Symbol in Table 4) | Acid Generator (represented by Symbol in Table 1) | Sensitivity (mJ/cm$^2$) |
|---|---|---|---|---|
| Example 22 | RESIN 1 | DRI 1 | PAG 5 | 15 |
| Example 23 | RESIN 2 | DRI 1 | PAG 5 | 60 |
| Example 24 | RESIN 3 | DRI 1 | PAG 5 | 50 |
| Example 25 | RESIN 4 | DRI 1 | PAG 5 | 61 |
| Example 26 | RESIN 5 | DRI 1 | PAG 5 | 90 |
| Example 27 | RESIN 1 | DRI 2 | PAG 5 | 22 |
| Example 28 | RESIN 2 | DRI 2 | PAG 5 | 71 |
| Example 29 | RESIN 5 | DRI 2 | PAG 5 | 38 |
| Example 30 | RESIN 2 | DRI 3 | PAG 5 | 54 |
| Example 31 | RESIN 2 | DRI 4 | PAG 5 | 38 |
| Example 32 | RESIN 2 | DRI 5 | PAG 5 | 71 |

What is claimed is:

1. A tert-butyl 4,4-bis(4'-hydroxyphenyl)pentoanoate compound of the following formula (I):

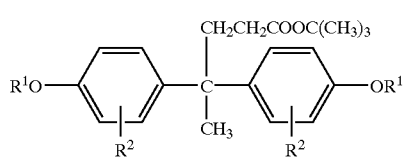

wherein each $R^1$ is a protective group capable of being readily eliminated under an acidic condition, and each $R^2$ is a hydrogen atom, a lower alkyl group or a lower alkoxy group.

2. A tert-butyl 4,4-bis(4'-hydroxyphenyl)pentoanoate compound of claim 1, wherein $R^1$ is a protective group selected from the group consisting of a t-butoxycarbonyl group, a t-butoxycarbonylmethyl group, a tetrahydropyranyl group, a methoxymethyl group, a diphenylmethyl group, a triphenylmethyl group, a trimethylsilyl group, a triethylsilyl group and a t-butyldimethylsilyl group.

3. A tert-butyl 4,4-bis(4'-hydroxyphenyl)pentanoate compound of the following formula (I):

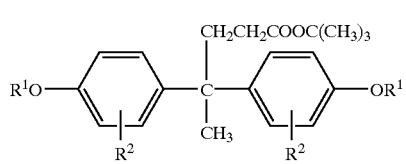

wherein each $R^1$ is a protective group capable of being readily eliminated under an acidic condition, and each $R^2$ is a hydrogen atom a lower alkyl group or a lower alkoxy group, produced by firstly treating the corresponding 4,4-(bis(4'-hydroxyphenyl) pentanoic acid with trifluoroacetic acid anhydride, reacting with t-butyl alcohol to obtain a t-butyl 4,4-bis(4'-hydroxyphenyl)pentanoate.of the formula (II):

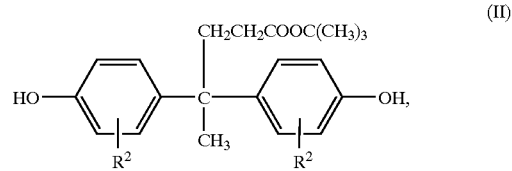

and replacing both of the hydrogen atoms of the OH groups with a protective group, $R^1$, to obtain the compound of formula I.

4. A positive resist material which is developable with an aqueous alkali solution, responsive to high-energy radiation and constituted of three components, (a) a poly (hydroxystyrene) resin in which at least part of the hydrogen atoms of the hydroxy groups are replaced by t-butoxycarbonyl groups, (b) a dissolution inhibitor and (c) an acid generator, with the three components (a), (b) and (c) having the weight proportions defined by the relations: $0.55 \leq a$, $0.07 \leq b \leq 0.40$, $0.005 \leq c < 0.15$, and $a+b+c=1$; said dissolution inhibitor (b) being a compound selected from the tert-butyl 4,4-bis(4'-hydroxyphenyl) pentanoate compounds of the following formula (I):

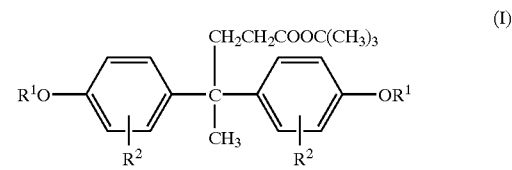

wherein each $R^1$ is a protective group capable of being readily eliminated under an acidic condition, and each $R^2$ is a hydrogen atom, a lower alkyl group or a lower alkoxy group.

5. The positive resist material of claim 4, wherein the poly(hydroxystyrene) resin is a monodisperse polymer obtained by a living polymerization method.

6. The tert-butyl 4,4-bis(4'-hydroxyphenyl)pentanoate compound of claim 1, wherein each $R^2$ is a hydrogen atom, methyl group, ethyl group, methoxy group or ethoxy group.

7. A tert-butyl 4,4-bis(4'-hydroxyphenyl)pentoanoate of the following formula (I):

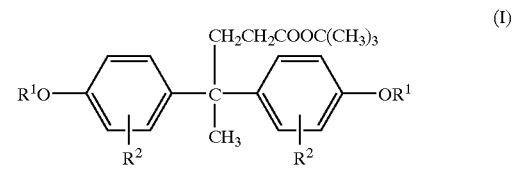

wherein each $R^1$ is a protective group capable of being readily eliminated under an acidic condition, and each $R^2$ is a hydrogen atom, a lower alkyl group or a lower alkoxy group, produced by treating a corresponding 4,4-bis(4'-hydroxyphenyl)pentanoic acid with trifluoroacetic acid anhydride, reacting the treated acid with t-butyl alcohol to obtain a compound of the formula II:

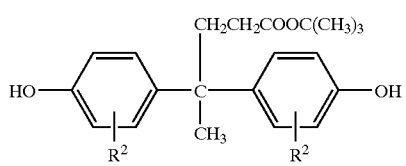

(II)

wherein $R^2$ has the meaning given above, purifying the compound of formula (II) and reacting the purified compound of formula (II) with an agent to add the protective groups, $R^1$.

8. A tert-butyl 4,4-bis(4'-hydroxyphenyl)pentoanoate compound of claim 7, wherein $R^1$ is a protective group selected from the group consisting of a t-butoxycarbonyl group, a t-butoxycarbonylmethyl gruop, a tetrahydropyranyl group, a methoxymethyl group, a diphenylmethyl group, a triphenylmethyl group, a trimethylsilyl gorup, a triethylsilyl group and a t-butyldimethylsilyl group.

9. A positive resist material which is developable with an aqueous alkali solution, responsive to high-energy radiation and constituted of three components, (a) a poly(hydroxystyrene) resin in which hydrogen atoms of the hydroxy groups are partly replaced by t-butoxycarbonyl groups, (b) a dissolution inhibitor and (c) an acid generator, with the three components (a), (b) and (c) having the weight proportions defined by the relations: $0.55 \leq a$, $0.07 \leq b \leq 0.40$, $0.005 \leq c < 0.15$, and $a+b+c=1$; said dissolution inhibitor (b) being a compound selected from the tert-butyl 4,4-bis(4'-hydroxyphenyl) pentanoate compounds of the formula (I):

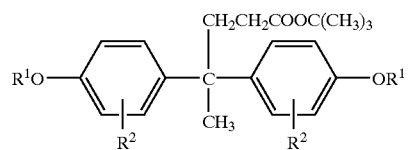

(I)

wherein each $R^1$ is a protective group capable of being readily eliminated under an acidic condition, and each $R^2$ is a hydrogen atom, a lower alkyl group or a lower alkoxy group. produced by treating a corresponding 4,4-bis(4'-hydroxyphenyl)pentanoic acid with trifluoroacetic acid anhydride, reacting the treated acid with t-butyl alcohol to obtain a compound of the formula II:

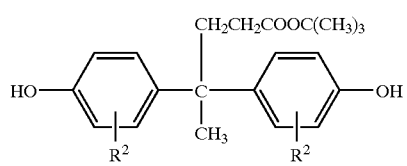

(II)

wherein $R^2$ has the meaning given above, purifying the compound of formula (II) and reacting the purified compound of formula (II) with an agent to add the protective groups, $R^1$.

10. The tert-butyl 4,4-bis(4'-hydroxyphenyl)pentanoate compound of claim 7, wherein the treatment of the corresponding 4,4-bis(4'-hydroxyphenyl)pentanoic acid is conducted with 3–5 moles of trifluoroacetic acid anhydride per mole of the acid.

11. The tert-butyl 4,4-bis(4'-hydroxyphenyl)pentanoate compound of claim 7, wherein the reaction of the treated acid is conducted with 3–5 moles of t-butyl alcohol per mole of the treated acid.

12. The tert-butyl 4,4-bis(4'-hydroxyphenyl)pentanoate compound of claim 7, wherein the treatment of the corresponding 4,4-bis(4'-hydroxyphenyl)pentanoic acid with trifluoroacetic acid anhydride and reaction of the treated acid with butyl alcohol is conducted in the presence of a solvent at $-10°$ C. to $+10°$ C.

13. The positive resist material of claim 4, wherein the poly(hydroxystyrene) resin, (a), has 10 to 50% of its hydrogen atoms replaced by t-butoxycarbonyl groups.

14. The positive resist material of claim 4, wherein the poly(hydroxystyrene) resin, (a), is a monodisperse system having a molecular weight of at least 10,000.

15. The positive resist material of claim 4, wherein the acid generator, (c), is an onium salt, diazo, benzyl tosylate, benzoin tosylate or triazine compound or mixture thereof.

16. The positive resist material of claim 4, wherein the acid generator, (c), is an onium salt of one of the following formulae:

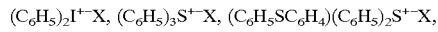
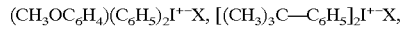

wherein X represents a p-toluenesulfonyl group, trifluoromethanesulfonyl group, hexafluoroantimonate group, hexafluorophosphate group, or a tetrafluoroborate group.

* * * * *